United States Patent
Simanovsky

(10) Patent No.: US 7,766,850 B2
(45) Date of Patent: Aug. 3, 2010

(54) DEROTATIONAL BRACE FOR TREATMENT OF IDIOPATHIC SCOLIOSIS

(75) Inventor: Naum Simanovsky, Zfon Yehuda (IL)

(73) Assignee: Hadasit Medical Research Services & Development Limited, Jerusalem (IL)

( * ) Notice: Subject to any disclaimer, the term of this patent is extended or adjusted under 35 U.S.C. 154(b) by 486 days.

(21) Appl. No.: 10/570,168

(22) PCT Filed: Sep. 5, 2004

(86) PCT No.: PCT/IL2004/000798

§ 371 (c)(1),
(2), (4) Date: Jun. 8, 2006

(87) PCT Pub. No.: WO2005/023157

PCT Pub. Date: Mar. 17, 2005

(65) Prior Publication Data

US 2007/0010768 A1    Jan. 11, 2007

(30) Foreign Application Priority Data

Sep. 5, 2003    (IL) ...................................... 157782

(51) Int. Cl.
*A61F 5/00*    (2006.01)

(52) U.S. Cl. ........................................... 602/19; 602/5

(58) Field of Classification Search .................. 602/19, 602/5, 18, 36, 38, 4, 32; 606/61, 54, 241, 606/55, 57, 58; 128/78, 95.1, 96.1, 874, 128/875, 869

See application file for complete search history.

(56) References Cited

U.S. PATENT DOCUMENTS

| | | | |
|---|---|---|---|
| 1,722,205 A * | 7/1929 | Freund ............................ | 2/44 |
| 3,420,230 A | 1/1969 | Ballard et al. | |
| 4,230,101 A | 10/1980 | Gold | |
| 4,715,362 A * | 12/1987 | Scott ........................... | 602/36 |
| 5,012,798 A | 5/1991 | Graf et al. | |
| 5,503,621 A | 4/1996 | Miller | |
| 5,599,286 A | 2/1997 | Labelle et al. | |
| 5,651,764 A | 7/1997 | Chiu | |
| 5,840,051 A | 11/1998 | Towsley | |
| 5,950,628 A * | 9/1999 | Dunfee ........................ | 128/874 |
| 6,605,052 B1 | 8/2003 | Cool et al. | |

FOREIGN PATENT DOCUMENTS

| | | |
|---|---|---|
| DE | 45207 | 11/1888 |
| DE | 66593 | 1/1893 |
| DE | 27 43 966 A1 | 4/1979 |

* cited by examiner

*Primary Examiner*—Kim M Lewis
(74) *Attorney, Agent, or Firm*—The Nath Law Group; Derek Richmond; Sung Yeop Chung

(57) ABSTRACT

A brace for correction of scoliosis is disclosed, comprising at least one thoracic shell element and a pelvic shell element and at least one working element having a main longitudinal axis to be oriented parallel to the trunk to be treated, anchored on one of its opposite ends to the thoracic shell element and on the other to the pelvic shell element, and having spring characteristics adapted to apply continuous de-rotational force about said longitudinal axis.

7 Claims, 6 Drawing Sheets

DEROTATIONAL BRACE FOR TREATMENT OF IDIOPATHIC SCOLIOSIS

CROSS-REFERENCE

Figure 1:
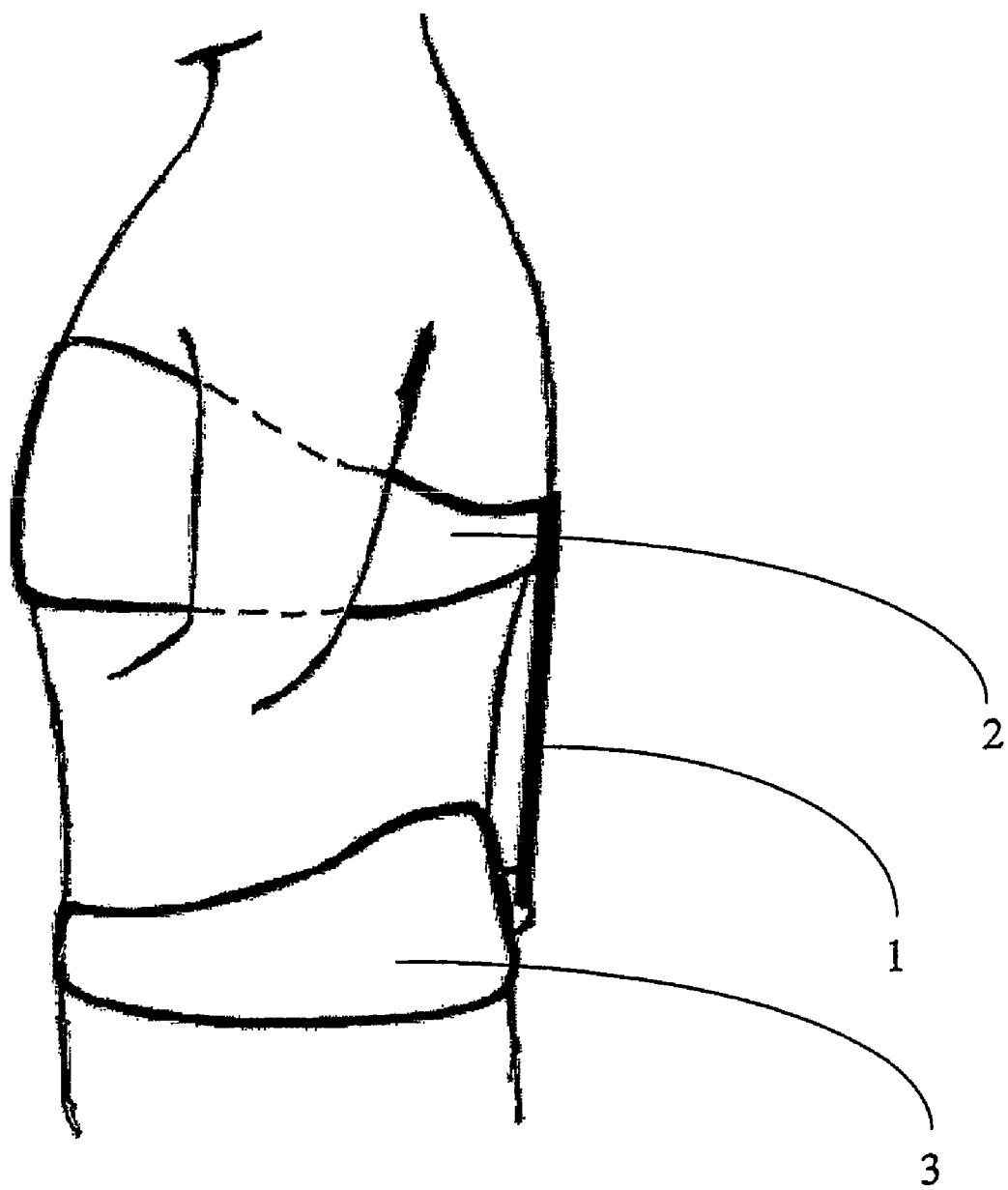

This is a National Phase Application filed under 35 U.S.C. 371 of International Application No. PCT/IL2004/000798, filed Sep. 5, 2004, the entire content of which is hereby incorporated herein by reference in its entirety.

FIELD OF THE INVENTION

The present invention generally relates to a de-rotation brace for treatment of idiopathic scoliosis, and to a method for treating scoliosis and idiopathic scoliosis.

BACKGROUND OF THE INVENTION

Scoliosis, known also by the terms idiopathic scoliosis, spinal curvature and lardoscoliosis) is a deviation from a normal spine in three directions or planes: frontal (coronal), lateral (sagittal) and transversal (axial). While ten percent of the population will have some spinal curvature, no more than three promilles require extensive medical treatment. Scoliosis may be present due to underlying muscle or nerve problems, a defect in bone formation or due to unknown reasons, i.e., idiopathic scoliosis. Idiopathic scoliosis, and particularly its adolescent type, may affect up to three percent of the adolescent population. One treatment is provided by a scoliosis brace, which is an orthosis adapted to hold the spine in a straighter position. The brace is prescribed by an orthopedic specialist and is usually worn constantly and continuously until bone growth has stopped.

As set forth above, scoliosis is a complex 3-D deformation of the trunk, spine and rib cage. From the clinical point of view, the most prominent feature of this complex deformity is a sideward curvature of the trunk accompanied by the rib's hump. In such cases a rib hump is still present and even progresses with all its consequences. The list of clinical problems associated with scoliosis goes far beyond the pure cosmetic complaints. It includes a distortion of the abdominal and chest organs and therefore an alteration of their functional capabilities, alteration of a normal gait with associated pelvic obliquity and many other functional and psychosocial difficulties.

Unlike congenital scoliosis, which is caused by congenital anomalies of the spinal structure, for the idiopathic type of scoliosis no congenital anomalies of vertebras or rib cage are identified. This may partially explain the fact that to date, despite numerous attempts to identify the exact cause for this pathology it has not been not found. Therefore, the evaluation of medical methods of treatment is complicated and often empirical, and is based on the personal experience and beliefs of the surgeon. In fact, the principals of treatment of scoliosis have remained basically unchanged for the last 70 years.

Inventions disclosed in the art basically include different kinds of devices that permit some preservation of the natural spinal movement without compromising the stable holding properties of the fixation system.

Idiopathic scoliosis is not an acute illness, but with time the vertebrae become secondarily deformed. Surgeons who treat scoliosis know about the deformation of the scoliotic vertebrae, this deformity is especially prominent in computer tomography evaluation. Apical vertebrae are the most deformed and they appear twisted on the axial CT images.

It is acknowledged that less then ten percent of patients with idiopathic scoliosis will need a surgical correction. Fortunately, most of the patients are diagnosed during the early stage of the scoliotic progression and can be treated conservatively. For this purpose, different types of externally applied corrective devices were developed.

The idea of bracing for scoliosis treatment dates back to ancient times. Many attempts to stop the progression of structural scoliotic curves were performed in the past: forcible horizontal traction and suspension, corsets, casts and a variety of braces.

Long-term follow-up studies of patients treated with the Milwaukee-like braces indicate that the main effect of the brace is to halt the progression of moderate-degree scoliotic curves. U.S. Pat. No. 4,230,101 to Gold for example introduces an improved Milwaukee-style brace comprising upright metal bars and small straps that apply pressure to the spine. One of the well-known problems with this treatment is the issue of compliance with brace wear.

The Boston brace system was introduced in 1971 by John Hall and Bill Miller and is known worldwide as the standard for brace treatment. It is designed to be "active" by means of constantly applied de-rotation forces, but these forces are produced by the static arrangement of the pads. U.S. Pat. No. 5,503,621 to Miller for example discloses a body brace which is a Boston-style brace made of a plastic body jacket that fits snugly around the body to exert pressure on the ribs and back, pushing the spine into a straighter position. These braces are considerably uncomfortable corset-like orthosis that apply non-constant and scattered twisting forces on the body of the patients. Moreover, permanent loss of the natural flexibility of the spine because of the solid fusion of the spinal column is the price paid to protect the surgically achieved correction. The data suggests that part-time brace use sometimes may be as effective as full-time use. Complete failure to use the brace, however, has an adverse prognosis. Control or net correction of idiopathic scoliosis treated by this brace was achieved in approximately 80% of the patients. But control of the curves with apexes above T7, triple curves, and curves in excess of 45 degrees appeared poor.

The Charleston bending brace, designed to be worn during sleep, was introduced in 1989 as an alternative to upright bracing but the effectiveness of the Charleston bending orthosis is even lower than the Boston brace. The average effectiveness for different types of bracing is 50% but compliance is suggested in the literature to be lower than for the Milwaukee brace.

Current indications for bracing scoliosis include children with at least one year or more of growth remaining, with curves of between 25 and 40 degrees and with apex of T8 or below and approximately 50% flexibility (Boston Brace course). In a prospective study of adolescent idiopathic scoliosis, female patients with curves between 25 and 35 degrees were treated with an underarm plastic brace. A successful outcome was obtained in 74% (curve progression no more than 5 degrees) compared to 34% of those who had no treatment. With increasing severity of the initially detected curve the prognosis for the outcome is worse.

Only recently have investigators began to search for true dynamic types of braces. One example of this may be the TriaC™ brace with a system of straps, but the amount of corrective forces that can be generated by this brace is limited and probably needs constant adjustment for effective use.

U.S. Pat. No. 5,599,286 to Labelle et al. discloses an elastic de-rotating orthopedic device, which applies a rotational force by means of stretchable strip or a plurality of such rubber-like strips. This corset is not strictly and firmly affixed to the body of the patient and thus applies for unfocused rotatory forces. Moreover, those forces are not homogenous and tend to decrease as time follows. Lastly, U.S. Pat. No. 5,840,051 to Towsley presents a flexible back and shoulder orthopedic brace for spinal applications. This orthosis contains body straps that are immobilized by an elongated trunk made of metal vertebrates stack affixed by means of two threaded poles. The spine of the patient is extended and pulled by the device along the main longitudinal axis of the device and only minimal rotatory forces are applied.

A cost-effective and convenient scoliosis brace, adapted for every day use which provides for pure and highly focused rotational forces at a predetermined and constant measure thus meets a long felt need.

SUMMARY OF THE INVENTION

The main difference between the brace according to the present invention and other types of braces is that in the currently presented brace, a considerable amount of the corrective de-rotational force is generated by a superstructure having as a key part a linear spring (or spring loaded) member applying a continuous corrective de-rotational force about its longitudinal axis, between an upper and a lower brace parts.

It is thus one embodiment of the present invention to provide a brace useful for providing a controlled and progressive correction of the scoliosis by using pure derotational forces (that can be determined during treatment by placing spring member having a force appropriate for the current condition of the spine), while retaining a high degree of freedom in 3-D movement of the spinal trunk of the patient (i.e., 'scoliosis brace'). This novel efficient scoliosis brace is divided into at least two parts, each of which is denoted hereto in the term 'shell element'. The brace is hence characterized by (i) a static brace assembly comprising an upper and lower brace parts (hereinafter will be referred to also as thoracic shell and pelvic shell elements, respectively); and, (ii) a working element having a main longitudinal axis to be oriented parallel to the trunk to be treated, anchored on one of its opposite ends to the thoracic shell and on the other to the pelvic shell.

The aforementioned working element has spring characteristics (or is spring loaded) adapted to apply continuous derotational forces about said longitudinal axis while retaining at least a partial freedom for coronal or sagittal movements of the patient.

Thus the present invention provides a brace for correction of scoliosis comprising:

a. at least one static thoracic shell element;
b. at least one static pelvic shell element; and,
c. at least one working assembly comprising a working element, having a main longitudinal axis to be oriented parallel to a trunk of the patient to be treated, said working element being anchored at one of its ends to the thoracic shell element and being anchored in its other end to the pelvic shell element;

wherein said working element has spring characteristics (or is spring loaded) adapted to apply continuous derotational forces about said longitudinal axis while retaining at least a partial freedom for coronal or sagittal movements of the patient.

It is also in the scope of the present invention to provide the hereto-defined brace, which is adapted to treat multi-apex types of scoliosis. This brace comprises a static brace assembly comprising a pelvic shell element and a plurality of 2 or 3 thoracic shell elements with at least one working element connecting between each shell element and another shell element.

According to one preferred embodiment the working element is characterized by comprising a twistable spring-like plate. The invention will be further described as using such spring type, although it is not limited to a plate type spring. A helical spring, a rod shaped spring, or any other type of spring capable of applying corrective de-rotational force about a longitudinal axis lying parallel to a patient trunk could be used as well without departing from the scope of the present invention. Moreover, the working assembly may be comprised of a plurality of working elements, arranged in bundles, stacks or located in an array of parallel elements.

It is also in the scope of the present invention, wherein the working assembly comprises at least two sets of anchoring assembly, each anchoring assembly comprises the following three ingredients: (i) an anchoring device; (ii) a set of lower and upper clutches, and (iii), at least one fastening screw. The anchoring device is adapted to be immobilized firmly to the thoracic shell, or to the pelvic shell either directly or through any other additional component. The set of lower and upper clutches is adapted to clasp the working element, in a recess formed in between, the width of said recess is adapted to receiving the width of the working element with a small surplus gap on both sides of the working element. Lastly, the fastening screw connects between said anchoring device, said lower clutch, working element and said upper clutch in such a manner that a planar hinge is provided, enabling the working element to transmit a corrective de-rotational force which acts to pivot the anchoring assembly and in turn the surface of the brace to which it is attached, in the desired direction for correcting the scoliosis while, said working element can pivot in a limited course about said fastening screw and parallel to the patient back, due to the small surplus gap in the recess, on both sides of the working element. This pivoting of the working element is useful for providing the patient with some freedom in the lateral movements of his back and for allowing a correction of the posture by allowing the patient spine to straighten during the treatment period when the top of the patient back is brought to a more straight position, above its bottom.

It is another object of the present invention to provide a most convenient and effective method for treating scoliosis by means of the scoliosis brace as defined in any of the above. After measuring curve dimensions and magnitude (by any acceptable measuring method e.g. on roentgen photos or through infra-red measuring methods) as a primary step for determining whether a specific patient is to be treated (according to scoliosis seriousness with respect to acceptable standards), this method comprises the following steps: (i) adapting a pelvic shell and a thoracic shell for a patient to be treated; (ii) adapting a working element to be connected between the shells; (iii) anchoring the working element between the shells to form a scoliosis brace; (iv) dressing the patient with the brace for a certain number of hours a day (e.g. 15 hours or e.g. 17 hours) such that the working element transmits a continuous corrective de-rotational force to the patient trunk through the brace shells; (v) tracing the patient from time to time as a follow-up for determining the scoliosis state, and replacing the working element if need rises for changing the corrective de-rotational force.

According to one embodiment of the method according to the present invention, the step of adapting a pelvic shell and a thoracic shell for a patient to be treated is performed by (a) enveloping the patient with a soft cast, in such a manner that it encompasses the patient from the pelvis and upwards, along the spinal trunk; (b) dividing said casted whole brace to form thoracic and pelvic brace portions; (c) shaping said thoracic and pelvic brace portions (so as to form shells having contact areas with the patient body useful for transmitting pressures as uniformly as can be achieved, and adapted to the patient body, e.g. by minimizing (cutting) the brace area in the regions were the working element is not intended to affect a pressure, or e.g. cutting the brace region facing the breast in case of a female patient; (d) cutting said shaped thoracic and pelvic brace portions, so a side opening is provided, allowing for removal of the brace from the patient body; (e) fitting zippers or other closing arrangements on the rims of said openings; (f) connecting anchoring devices on the shells and (g) clutching a working element by said anchoring devices.

According to various embodiments of the present invention any of the brace upper and lower portions may further be provided with a reinforcement strip extended from the connection region between the anchoring device and the brace along certain regions of the brace and aimed to divide the pressure transmitted from the working element to the shell element at their connection over a wider area of the shell element. The reinforcement strip can be incorporated to the brace inside the cast as an inner layer of the shell element, or on its surface, and it could be made of any elastic material, e.g. a plastic strip, or a thin steel strip.

Thus, according to one embodiment the present invention provides a method for treating scoliosis, comprising:

a. enveloping the patient with a soft cast, in such a manner that it encompasses the patient from the pelvis and upwards, along the spinal trunk;

b. dividing said casted whole brace to form thoracic shell element and a pelvic shell;

c. optionally shaping said thoracic and pelvic shell elements to a desired shape (e.g. for improving pressure distribution, or e.g. when the shape received by the casting comprise surplus portions which may unnecessarily disturb the patient);

d. cutting said thoracic and pelvic shell elements, so a side opening is provided on each;

e. fitting attachers on the rims of said openings;

f. connecting anchoring elements to the thoracic and pelvic shell elements; and, g. clutching a working element having a main longitudinal axis parallel to a trunk of the patient to be treated, to said anchoring devices in a manner that said working element has spring characteristics adapted to apply continuous derotational forces along the said longitudinal axis while retaining at least a partial degree of freedom for coronal or sagittal movements of the patient wearing the brace.

According to another embodiment the present invention provides a method for treating scoliosis, comprising:

a. enveloping the patient with a soft cast, in such a manner that it encompasses the patient at the pelvis area to form a pelvic shell element;

b. enveloping the patient with a soft cast, in such a manner that it encompasses the patient at the thoracic area, to form a thoracic shell element;

c. optionally shaping said thoracic and pelvic shell elements to a desired shape (e.g. for improving pressure distribution, or e.g. when the shape received by the casting comprise surplus portions which may unnecessarily disturb the patient);

d. cutting said thoracic and pelvic shell elements, so a side opening is provided on each;

e. fitting attachers on the rims of said openings;

f. connecting anchoring elements to the thoracic and pelvic shell elements; and, g. clutching a working element having a main longitudinal axis parallel to a trunk of the patient to be treated, to said anchoring devices in a manner that said working element has spring characteristics adapted to apply continuous derotational forces along the said longitudinal axis while retaining at least a partial degree of freedom for coronal or sagittal movements of the patient wearing the brace.

According to another embodiment the present invention provides a method for treating scoliosis, comprising:

a. adapting a prefabricated pelvic shell element to a patient to be treated, from a plurality of measures of prefabricated pelvic shell elements;

b. adapting a prefabricated thoracic shell element to a patient to be treated, from a plurality of measures of prefabricated thoracic shell elements;

c. optionally shaping said thoracic and pelvic shell elements to a desired shape (e.g. for improving pressure distribution, or e.g. when the shape received by the casting comprise surplus portions which may unnecessarily disturb the patient);

d. adapting a working element to the patient to be treated;

e. clutching the working element to anchoring devices connected to said shell elements in such that spring characteristics of said working element apply continuous derotational forces along a longitudinal axis of the working element while retaining at least a partial degree of freedom for coronal or sagittal movements of the patient.

It is yet in the scope of the present invention to provide a method especially adapted for treating multi-apex type scoliosis. By this aspect the method is directed also to a case wherein, a plurality 2 or 3 thoracic shell elements are provided (either by selecting and adapting them to the patient from a plurality of measures of prefabricated shell elements, or by casting them on the patient body either separately or as one casting then dividing it by cutting) and wherein each of the thoracic shell elements is connected to another or to a pelvic shell element through a working element.

BRIEF DESCRIPTION OF THE INVENTION

Figures 2, 3:
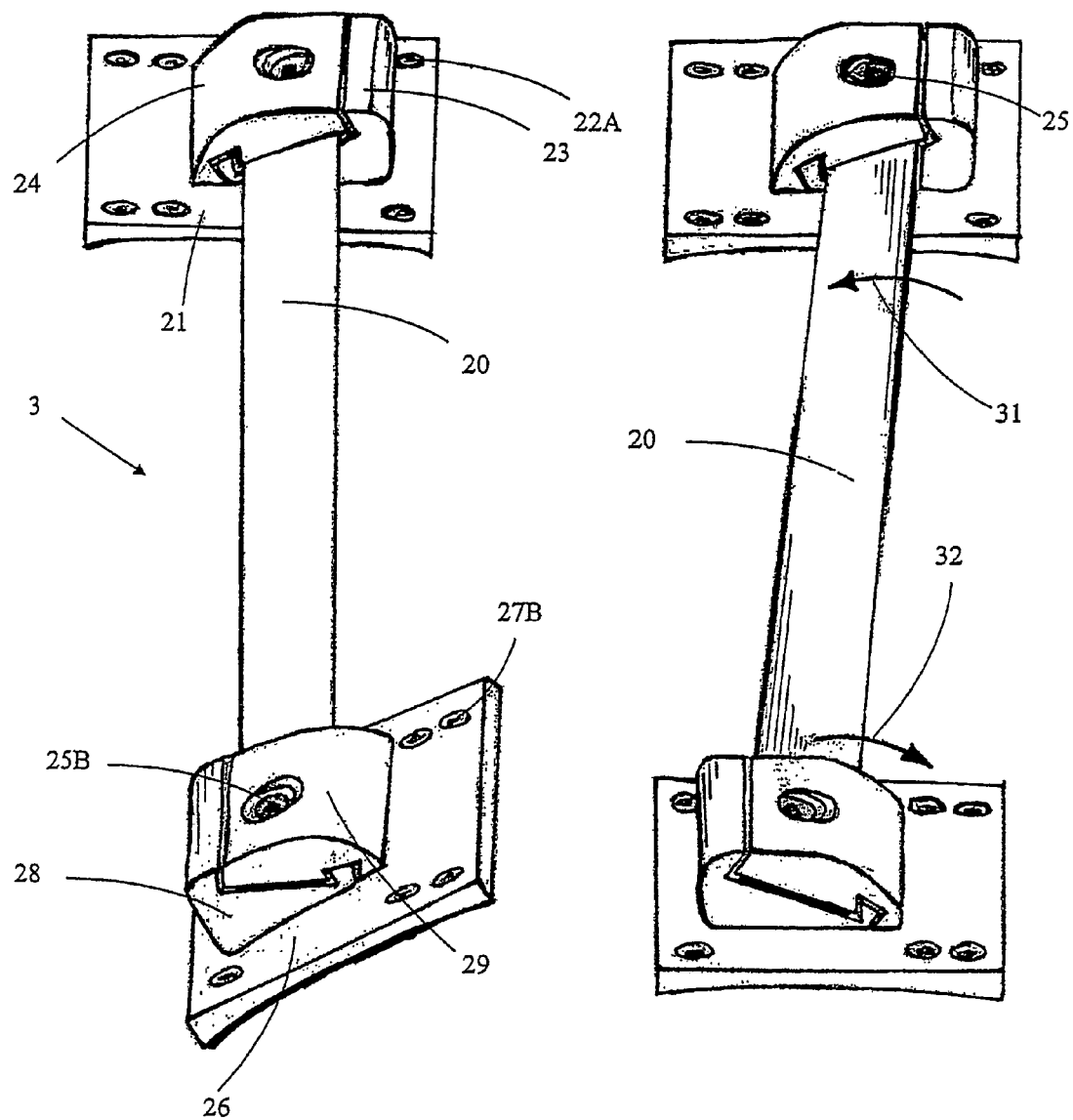
Figure 4:
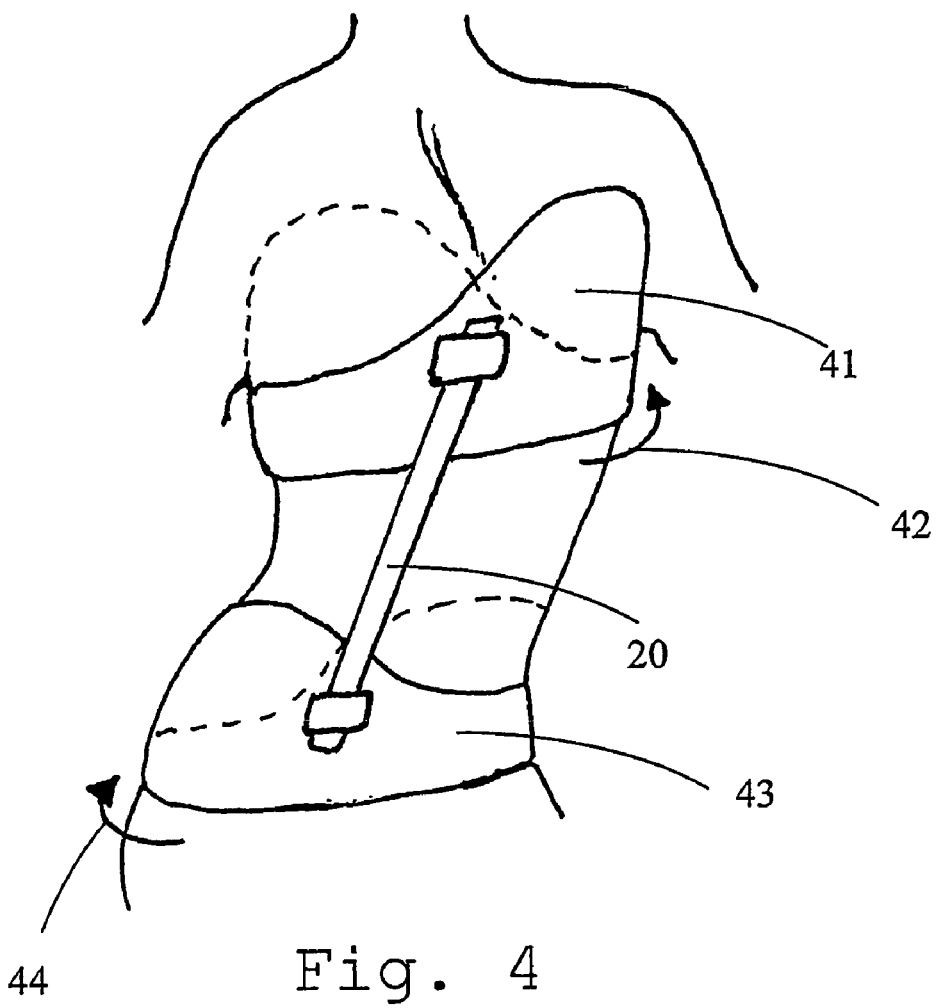
Figure 5:
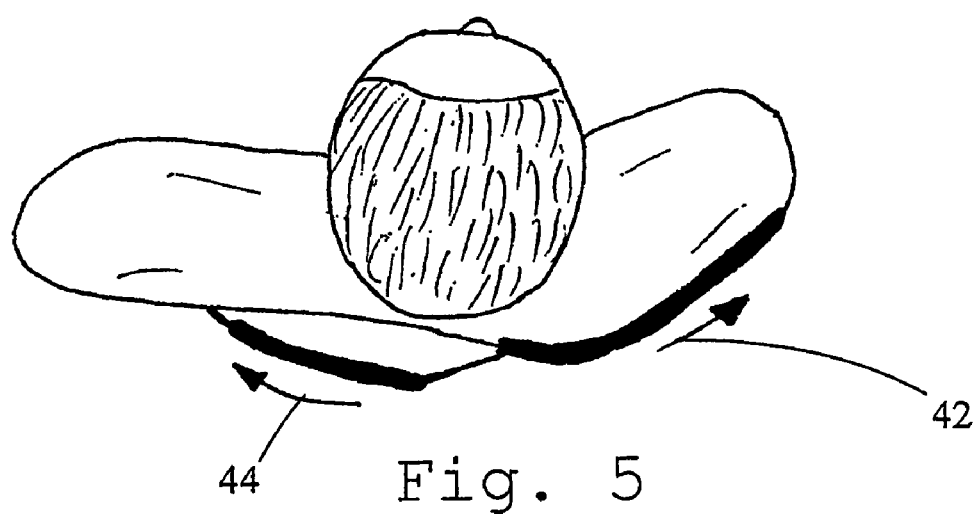
Figure 6:
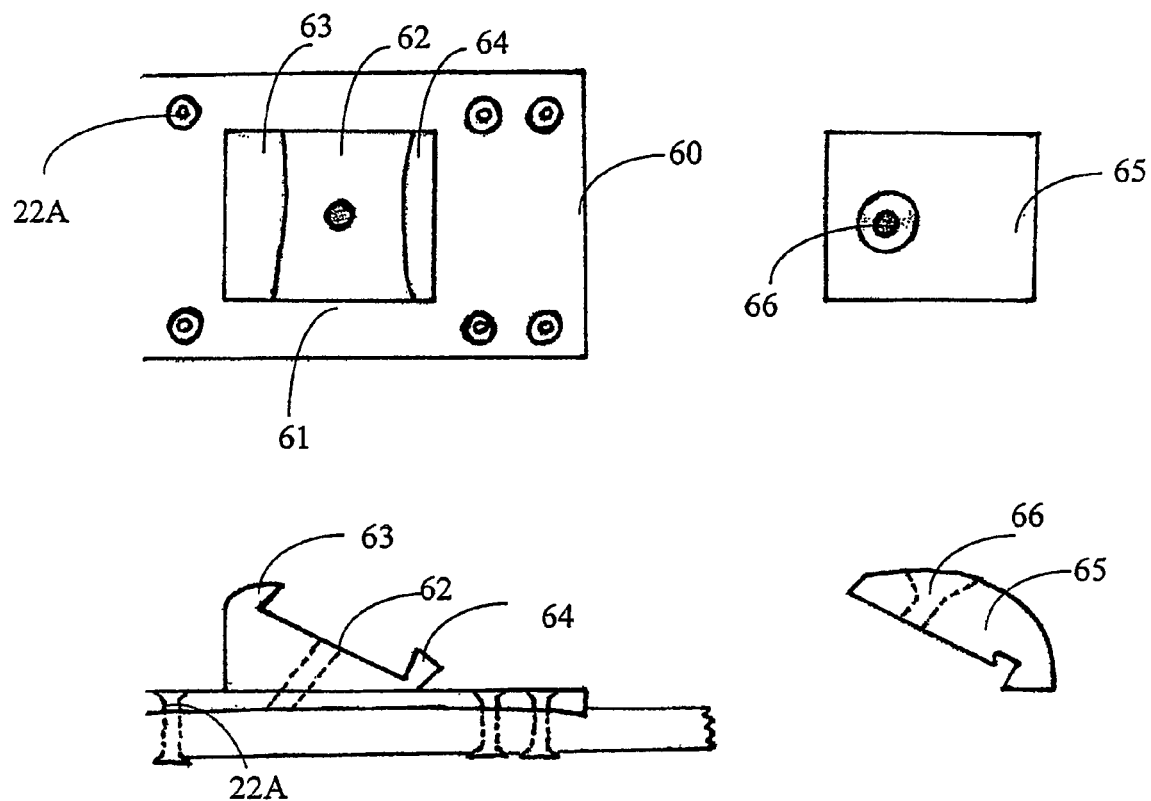
Figure 7:
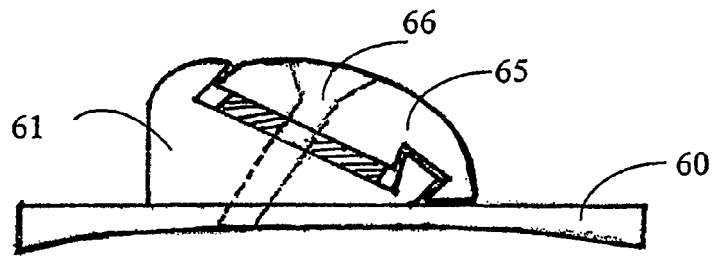
Figure 8:
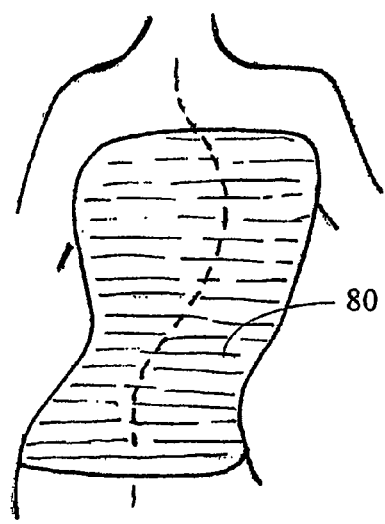
Figure 9:
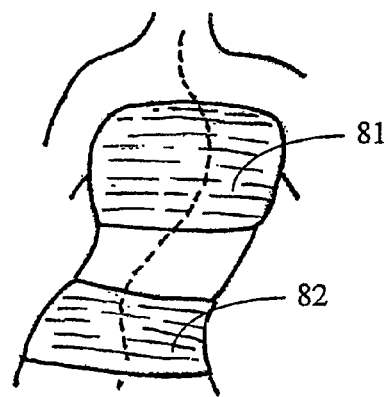
Figure 10:
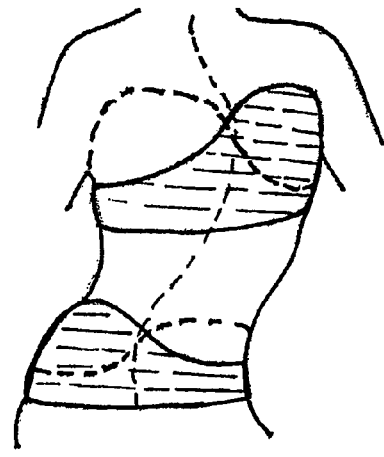
Figure 11:
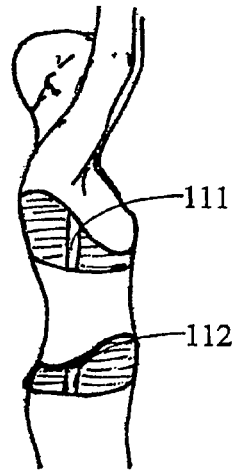
Figure 12:
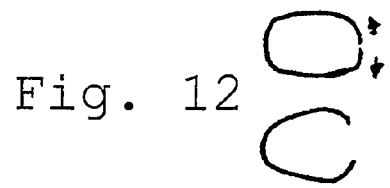
Figure 13:
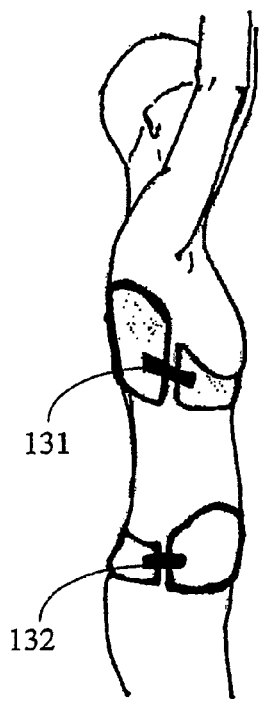
Figure 14:
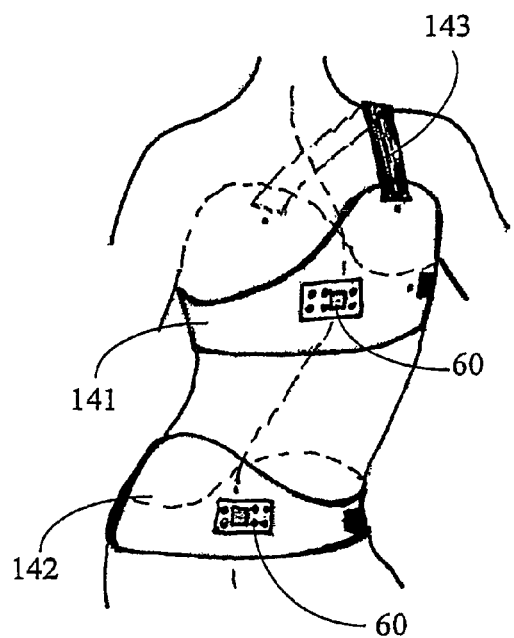

In order to understand the invention and to see how it may be implemented in practice, a preferred embodiment will now be described, by way of non-limiting example only, with reference to the accompanying drawing, in which FIG. 1 schematically presents a side view of a patient wearing the scoliosis brace according to one embodiment of the present invention;

FIG. 2 schematically presents a top view of the working assembly in a rest configuration;

FIG. 3 schematically presents a top view of the same working assembly in a rotated configuration;

FIG. 4 schematically presents a front view of a patient back with a scoliosis brace according to said embodiment of the present invention;

FIG. 5 schematically presents a top view of a patient wearing a scoliosis brace according to said embodiment of the present invention;

FIG. 6 schematically presents a top view, a lateral cross section and perspective view of the various ingredients of the anchoring assembly of the working assembly;

FIG. 7 schematically presents a lateral cross section of the assembled anchoring assembly of the working assembly;

FIG. 8 schematically presents a front view of the whole scoliosis brace;

FIG. 9 schematically presents a front view of the divided scoliosis brace;

FIG. 10 schematically presents a front view of the shaped scoliosis brace;

FIG. 11 schematically presents a side view of a patient wearing the scoliosis brace, wherein said brace contains side openings;

FIG. 12 schematically presents a top view of the scoliosis brace containing side openings in open and closed configurations;

FIG. 13 schematically presents a side view of a patient wearing the scoliosis brace, wherein said brace contains zippers; and, FIG. 14 schematically presents a front view of a patient wearing the scoliosis brace, wherein the anchoring devices are immobilized on top of the two portions of the brace.

DETAILED DESCRIPTION OF THE INVENTION

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the general principles of the present invention have been defined specifically to provide a scoliosis brace useful for providing a controlled and progressive correction of the scoliosis by using pure derotational forces, while retaining a high degree of freedom in 3-D movement of the spinal trunk of the patient.

The term 'idiopathic scoliosis' refers in the present invention to any malfunction of the trunk and/or the spinal column and to the various variants and subtypes, especially adolescent scoliosis.

The term 'the brace' refers in the present invention to any orthosis as hereto described and defined, adapted to treat said idiopathic scoliosis by means of a brace having a working element characterized by spring properties that inter alia are adapted to apply pure and constant derotational (i.e. either rotational and/or derotational) forces.

The invention thus includes two major parts: a dynamic brace, which is adapted for treatment of adolescent idiopathic scoliosis; and means that are adapted to provide a controlled progressive correction of the scoliosis by using pure derotational forces produced by the said dynamic brace.

The aforementioned brace comprises two major assemblies: a static assembly made from a thoracic and pelvic shell elements both elements are adapted to anchor the orthosis to the patient; and a working assembly comprising at least one working element having spring properties.

The static assembly is comprised of an external shell, built from two separate units: thoracic (i.e., upper) unit and pelvic (i.e., lower) unit. These two units are made of any kind of suitable material incorporating both significant elasticity and noticeable rigidity, e.g., high-density polypropylene (HDPP) polymer or copolymer, polyurethane containing thermosetic/thermoplastic polymers or copolymers etc. This external shell is removable by a means of at least one lateral opening.

The working assembly comprises at least one principal working element, which is in communication with at least two connecting devices, one located in the upper portion of the element and the second located in its lower portion. Said working element is characterized by spring properties that produce a rotational effect on the spine.

The working element connects between the two units of the external shell. To achieve a continuous (e.g., constant and homogenous) effect of derotation, the plate is molded in a twisting manner and then fixed by its ends to the anchoring parts of the device. The spring properties and rebound effect of the working element permit the continuous dynamic derotational effect on the trunk and the spinal column. The fixation of the working element to the external shell units is designed in such a way that free movements of the trunk are preserved.

According to another embodiment, the working element is characterized by a rigid pole like member located parallel to the trunk to be treated. Said rigid pole-like member is in communication with at least one working member (e.g., a spring, a torque pole etc). Said working member is either integrated to the pole-like member, or located at the end of the pole-like member, at the joint connecting the said pole-like member and one of the brace's shells. According to another embodiment, the rigid working element is exceeded to two spring-like units, each of which located in an end of the member in such a manner that it interconnects said element with the thoracic shell and the pelvic shell.

The measure of derotational forces applied may be adjusted during the follow up period by exchanging the working element by another one with a different thickness or stiffness (i.e. resulting in different spring characteristics). The other way to change the amount of de-rotational forces is to adjust the degree of the initial twisting of the longitudinal spring plate. The design of the device will permit preservation of almost all of the natural mobility of the trunk. The design of the brace allows a free sideway translation of the shoulders and upper back relative to the lower back and pelvis during the treatment process. This quality is essential to improve the spinal balance in cases of unbalanced spine at the beginning of the treatment process.

Reference is made now to FIG. 1, presenting a schematic side view of the idiopathic scoliosis according to one embodiment of present invention comprising a working assembly (1) located in an erect orientation adjacent to the truck. The working assembly (1) is anchored to the two parts of the static assembly, e.g., the thoracic shell (2) and the pelvic shell (3).

Reference is made now to FIG. 2, presenting a top view of the working assembly (3) comprising a working element (20) and two anchoring devices (21) and (26). It is according to one preferred embodiment of the present invention wherein the working element is characterized by a linear plate shape having an approximately rectangular shape or any other polygonal shape. Nevertheless, it is well in the scope of the present invention wherein said working assembly comprises a plurality of N working elements, wherein N is an integer number between 1 to 100, and further wherein the working element is characterized by a shape selected from polygonal, rounded, spring-like or any combination thereof. The working element is made of metal alloy, stainless steel, polymers, composite materials or any combination thereof. Its dimensions may vary from a few centimeters to about 75 cm, preferably its length is approximately equal to the distance between the thoracic portion and the pelvic portion of the back of the patient. The linear plate-like working assembly may be characterized by a stack configuration, whereat a plurality of leaf-like plates are stacked together. Additionally or alternatively, the working element is a bundle of pole-like elements, wherein the number of the elements determines both the elasticity and the derotational forces characterizing the working element.

Reference is still made to FIG. 2, presenting the anchoring devices (21) and (26) that are attached to the working element (20) by means of the lower and upper clutch members (23, 24), respectively and lower and upper clutch members (29, 28), respectively. The anchoring devices (21, 26) include the means to be firmly entrapped to the brace, e.g., by means of 6 screws of fasteners located in holes such as those denoted in signs (22A) and (27A). Upper clutch member (24) is firmly attached to one end portion of the working element (20), to the lower clutch member (23) and to anchoring device (21) by means of a screw (25A), by a plurality of fasteners or by any other reversible means. Similarly, upper clutch (29) is fastened to the opposite portion of the working element (20), to the lower clutch (28) and to the anchoring device (26) by a means of a screw (25B).

Reference is made now to FIG. 3, presenting a top view of the said working assembly (1), wherein the working element (20) is rotated so that the thoracic portion is twisted towards the left direction (31) while the pelvic portion is forced towards the right direction (32).

Reference is made now to FIG. 4, presenting a view of a patient's back having a typical scoliosis to be treated. Said patient is wearing the scoliosis brace according the present invention. The thoracic portion of the back is thus forced in the corrective direction shown by arrow (42) while the pelvic portion is forced in the corrective direction shown by arrow (44) by means of the linear working element (20), which is attached on its upper portion to the thoracic shell of the brace (41), and in its lower portion to the pelvic shell of the brace (43). It is acknowledged that one or more of the brace's portion may be shaped in an unequal manner. Hence, the right portion of the thoracic brace is characterized by significantly more surface area, while the left portion of the pelvic brace (43) is wider than its right portion, such that the portions of the brace which transmit the force of the working element to the patient body are made wider for more even distribution of the forces acting on the patient body. From the same reason, in the frontal side of the brace shells (hidden in this figure by the patient body), the thoracic shell of the brace has a larger area on its left side comparing to the area on its right, and the pelvic shell of the brace has a larger area on its right side comparing to the area on its left, since the direction of the forces on the frontal portions of the brace shells act in a similar tendency with the forces on the rear side, i.e. exerting forces on the left of the patient chest and on the right of its pelvis. More even circumferential distribution of the forces acting on the patient body is thus provided.

FIG. 5 schematically presents the same patient and brace illustrated by FIG. 4, from a top view. The thoracic shell member of the brace is forced by the working element in the direction shown by the arrow (42) while the pelvic shell member of the brace is forced by the working element in the direction shown by arrow (44).

Reference is made now to FIGS. 6 and 7, presenting the anchoring assembly from top view, perspective view and in a lateral cross section. According to yet another embodiment of the present invention, the anchoring device (60) is characterized by a rectangular shape comprising a plurality of bores (e.g., 22A) adapted to fit screws or any other fastening members. Those screws or other fasteners immobilize the anchoring device to the brace. If the rotational forces are directed rightwards, the lower (61) and upper (65) clutches are located somewhat leftwards from the center of the anchoring device (60) and vice versa, providing for maximum lever means to the working element (not shown). Said working element is adapted to be accommodated in between the lower (61) and upper (65) clutches while a fastening screw (66) is locked firmly in said "sandwich". The lower clutch (61) is preferably comprised of a recess (62), wider than the width of the working element, so the element has a predetermined freedom to rotate about the fastening screw (66) due to gaps (62a) and (62b) on both sides of the working element, as can be seen in FIG. 7. Said recess is defined by a plurality of protrusions (63) and (64), that fit to one or more recesses located on the upper clutch (65). While the upper surface of the anchoring plate is linear, its lower surface, facing the brace, may be non-linear, e.g., curved, having a trapeze-like shape etc. Reference is made now to FIG. 7, presenting the anchoring assembly from a lateral cross section view, wherein the working element (20) is accommodated in between the lower (61) and upper (65) clutches by means of a fastening screw (66), hence affecting the anchoring device (60) to be twisted towards a predetermined direction.

Reference is made now to FIGS. 8 to 14, presenting lateral views, side view and top view of a patient wearing the scoliosis brace according to present invention. These Figures also present at least one embodiment of the method for using said novel scoliosis brace as defined and described in the present invention.

After measuring the scoliosis curve dimensions and its magnitude, the characteristics of the working element are calculated and said element is adapted to the patient to be treated. Said measurement of the spine is usually provided by CT scans, X-ray pictures etc. Reference is made now to FIG. 8, presenting the step whereat the patient is enveloped with a soft cast. The term "soft cast" refers in the present invention to any commercially available soft cast materials; gypsum or any other gypsum-like materials; plastics and polymers such as HDPP, polylactic acid (PLA) derivatives, polyurethanes; rubbers; composite materials; cloth or fabrics; metal frames or any combination thereof. The brace may be made from a continuous material or may comprise a plurality of holes and openings. Said newly formed envelope (80) encompasses the patient from his pelvis and upward, along the entire length of the spinal trunk.

Reference is made now to FIG. 9, presenting the step whereat the casted whole brace is divided into at least two portions: to form a thoracic brace (81) and a pelvic brace (82). It is in the scope of the present invention wherein said divided cast comprises three or more portions. This multi-portional brace may be provided in treatment of patients having more than one curve.

Reference is made now to FIG. 10, presenting the step of shaping the thoracic brace and/or a pelvic brace in an unequal manner, so the surface of the brace is wider along the direction of the derotational forces. Subsequently, reference is made to FIG. 11, presenting the step of putting inserting those shaped portions of the brace in its side, so that side openings (111) and (112) are provided. Those openings are also illustrated in FIG. 12 in a top view, showing a closed and an open configuration of the sliced brace.

Reference is made now to FIG. 13, presenting yet another side view of the patient the step of fitting a plurality of attachers (131) and (132) on the rims of said openings. Those attachers may be selected from zippers, laces, commercially available Velcro zippers, buckles, clasps etc.

Reference is made now to FIG. 14, presenting a front view of the patient, whereat the anchoring device (60) are immobilized on top of the two portions of the brace (141 and 142). Optionally, at least one enforcing strip (143) is now provided to support one or more portions of the brace.

Finally, the working element is clutched by means of the immobilized anchoring devices and clutches and the pure and constant de-rotatory forces are applied towards specifically determined locations along the patient's curved trunk.

The invention claimed is:

1. A brace for correction of scoliosis comprising a thoracic shell element, a pelvic shell element, and a working element having rotational spring characteristics and a main longitudinal axis, said thoracic and pelvic shell elements comprising anchoring devices adapted to anchor opposite ends of said working element thereto such that it is oriented, at least while a patient is wearing said brace, parallel to the trunk to be treated, said working element being designed to be twisted about its axis before the wearing such that the working element applies, during the wearing, a continuous derotational force to the trunk about said longitudinal axis due to the twisting.

2. The brace according to claim 1, wherein the working element is a twistable plate having spring characteristics configured for applying said derotational force about the longitudinal axis.

3. The brace according to claim 1, wherein the at least one working element is a part of a working assembly comprising at least two sets of anchoring assemblies, each of which comprises:
   a. an anchoring device adapted to be immobilized on the thoracic shell element, the pelvic shell element or any other brace portion;
   b. a set of lower and upper clutches adapted to clasp the working element in a recess formed in between and adapted to receiving the end of the working element with a surplus gap on both sides; and
   c. a fastening screw, communicating between said anchoring device, said lower clutch, working element and said upper clutch in such a manner that a planar hinge is provided; so said working element is free to pivot around said hinge in a controlled course, parallel to the patient back.

4. The brace according to claim 1, wherein the working element is a rigid elongate member located parallel to the trunk to be treated; said elongate member being in communication with at least one working member which is either integrated to said elongate member, or located at the end of the elongate member in such a manner that it connects said elongate member with one of the brace's shell elements.

5. The brace according to claim 4, wherein the rigid working element comprises at least two derotation units, each having spring characteristics configured for applying said derotational force about the longitudinal axis, in such a manner that at least one unit connects the upper end portion of the member with the thoracic shell and at least one unit connects the lower end portion of the member with the pelvic shell.

6. A method for treating scoliosis of a patient, the method comprising;
   (a) providing a brace comprising:
      (i) a thoracic shell element;
      (ii) a pelvic shell element; and
      (iii) a working element having rotational spring characteristics and a main longitudinal axis,
   said thoracic and pelvic shell elements comprising anchoring devices adapted to anchor opposite ends of said working element thereto such that it is oriented, at least while a patient is wearing said brace, parallel to the trunk to be treated;
   (b) twisting said working element about its axis before the wearing such that the working element applies, during the wearing, a continuous derotational force to the trunk about said longitudinal axis due to the twisting;
   (c) dressing the patient with the brace for a predetermined number of hours a day such that the working element transmits a continuous corrective derotational force to the patient trunk through the brace shells; and
   (d) tracing the patient from time to time as a follow-up for determining the scoliosis state, and replacing the working element for changing the corrective de-rotational force as needed.

7. The method for treating scoliosis according to claim 6, wherein the scoliosis brace is adapted to the patient by casting the pelvic shell or the thoracic shell on the patient body.

* * * * *